United States Patent
Thiel et al.

(10) Patent No.: US 6,679,939 B1
(45) Date of Patent: Jan. 20, 2004

(54) FRACTIONAL CONDENSATION OF A PRODUCT GAS MIXTURE CONTAINING ACRYLIC ACID

(75) Inventors: Joachim Thiel, Neustadt (DE); Jürgen Schröder, Ludwigshafen (DE); Gerhard Nestler, Ludwigshafen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/926,042

(22) PCT Filed: Feb. 28, 2000

(86) PCT No.: PCT/EP00/01630

§ 371 (c)(1),
(2), (4) Date: Aug. 20, 2001

(87) PCT Pub. No.: WO00/53561

PCT Pub. Date: Sep. 14, 2000

(30) Foreign Application Priority Data

Mar. 6, 1999 (DE) .......................... 199 09 923
May 28, 1999 (DE) .......................... 199 24 532

(51) Int. Cl.$^7$ ............................... B01D 47/14
(52) U.S. Cl. ....................... 95/210; 95/213; 96/299; 202/158; 203/39; 261/113; 261/114.2; 261/114.5
(58) Field of Search ................. 95/237, 211, 213, 95/210; 96/299; 202/158; 203/39; 261/114.2, 114.3, 114.5, 114.1, 113, 114.4

(56) References Cited

U.S. PATENT DOCUMENTS

| | | | |
|---|---|---|---|
| 3,872,009 A | | 3/1975 | Thijssen |
| 3,932,500 A | | 1/1976 | Duembgen et al. |
| 3,954,854 A | | 5/1976 | Gehrmann et al. |
| 4,156,633 A | * | 5/1979 | Horlenko et al. |
| 4,493,719 A | | 1/1985 | Wintermantel et al. |
| 5,244,604 A | * | 9/1993 | Miller et al. |
| 5,366,666 A | * | 11/1994 | Chuang et al. |
| 5,407,605 A | * | 4/1995 | Resetarits et al. |
| 5,426,221 A | | 6/1995 | Willersinn |
| 5,504,247 A | | 4/1996 | Saxer et al. |
| 5,521,264 A | * | 5/1996 | Mehra et al. |
| 5,637,222 A | * | 6/1997 | Herbst et al. |
| 5,733,075 A | | 3/1998 | Basteck |
| 5,739,391 A | | 4/1998 | Ruppel et al. |
| 5,821,390 A | | 10/1998 | Ruppel et al. |
| 6,051,736 A | * | 4/2000 | Schraut et al. |
| 6,089,550 A | * | 7/2000 | Petschauer et al. |
| 6,131,891 A | * | 10/2000 | Resetarits et al. |
| 6,395,140 B1 | * | 5/2002 | Herbst et al. |
| 6,433,222 B1 | | 8/2002 | Eck et al. |
| 6,436,245 B1 | * | 8/2002 | Nishimura et al. |
| 6,448,439 B1 | | 9/2002 | Eck et al. |
| 6,458,989 B1 | * | 10/2002 | Aichinger et al. |
| 2001/0016668 A1 | * | 8/2001 | Mitsumoto et al. |
| 2001/0025122 A1 | * | 9/2001 | Hirao et al. |
| 2002/0134660 A1 | * | 9/2002 | Sakamoto et al. |
| 2003/0019737 A1 | * | 1/2003 | Matsumoto et al. |
| 2003/0028052 A1 | * | 2/2003 | Hirao et al. |

FOREIGN PATENT DOCUMENTS

| | | |
|---|---|---|
| DE | 21 36 396 | 2/1973 |
| DE | 24 07 236 C2 | 9/1975 |
| DE | 26 06 364 | 9/1977 |
| DE | 41 01 879 A1 | 7/1992 |
| DE | 43 08 087 A1 | 9/1994 |
| DE | 197 40 252 A1 | 3/1999 |

(List continued on next page.)

*Primary Examiner*—Duane S. Smith
(74) *Attorney, Agent, or Firm*—Oblon, Spivak, McClelland, Maier & Neustadt, P.C.

(57) ABSTRACT

In a process for the fractional condensation of an acrylic acid-containing product gas mixture of a gas-phase partial oxidation of $C_3$ precursors of acrylic acid with molecular oxygen under heterogeneous catalysis, the separation column used contains both dual-flow trays and hydraulically sealed cross-flow trays as baffles having separation activity.

19 Claims, 1 Drawing Sheet

FOREIGN PATENT DOCUMENTS

| | | |
|---|---|---|
| DE | 197 40 253 A1 | 9/1999 |
| DE | 198 14 375 A1 | 10/1999 |
| DE | 198 14 421 A1 | 10/1999 |
| DE | 198 14 449 A1 | 10/1999 |
| DE | 198 33 049 A1 | 1/2000 |
| DE | 199 09 923 A1 | 3/2000 |
| EP | 0 097 405 A1 | 1/1984 |
| EP | 0 098 637 A1 | 1/1984 |
| EP | 0 105 524 A2 | 4/1984 |
| EP | 0 305 316 A2 | 3/1989 |
| EP | 0 616 998 A1 | 9/1994 |
| EP | 0 700 714 A1 | 3/1996 |
| EP | 0 700 893 A1 | 3/1996 |
| EP | 0 765 956 A1 | 4/1997 |
| FR | 2 668 946 | 5/1992 |
| JP | 3-178949 | 8/1991 |
| WO | WO 84/00118 | 1/1984 |
| WO | WO 97/45184 | 12/1997 |

\* cited by examiner

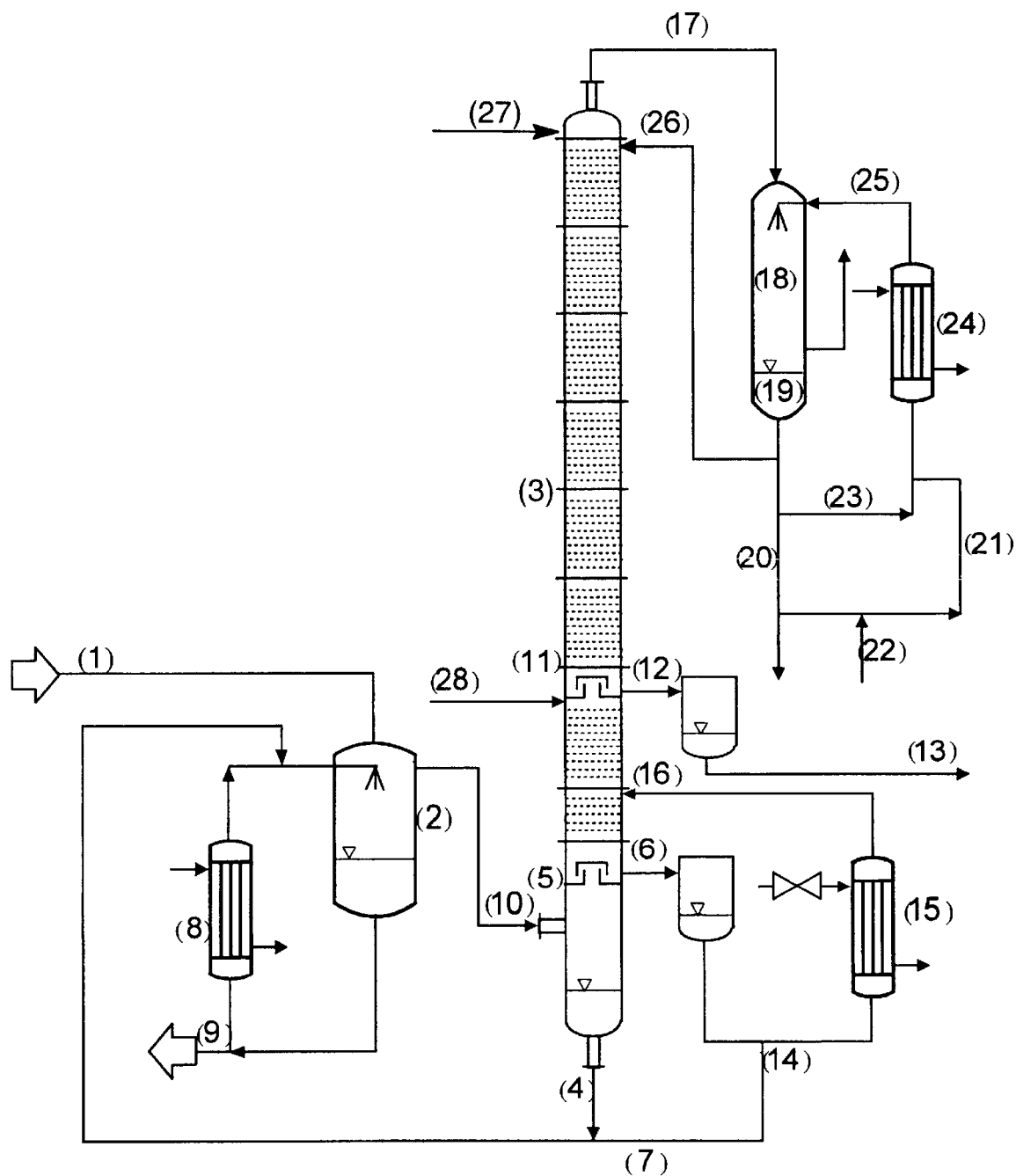

FRACTIONAL CONDENSATION OF A PRODUCT GAS MIXTURE CONTAINING ACRYLIC ACID

BACKGROUND OF THE INVENTION

The invention relates to a process for the fractional condensation of an acrylic acid-containing product gas mixture of a gas-phase partial oxidation of $C_3$ precursors of acrylic acid with molecular oxygen under heterogeneous catalysis precursors of acrylic acid with molecular oxygen under heterogeneous catalysis in a separation column containing hydraulically sealed cross-flow trays as baffles having separation activity.

Acrylic acid is an important intermediate which is used, for example, in the preparation of polymer dispersions.

Acrylic acid is obtainable, inter alia, by gas-phase partial oxidation of $C_3$ precursors of acrylic acid with molecular oxygen under heterogeneous catalysis over solid catalysts at elevated temperatures. The term "$C_3$ precursors" of acrylic acid covers those chemical compounds which are formally obtainable by reduction of acrylic acid. Known $C_3$ precursors of acrylic acid are, for example, propane, propene and acrolein. However, compounds such as propionaldehyde or propionic acid are also among the $C_3$ precursors. Starting from them, the gas-phase partial oxidation with molecular oxygen under heterogeneous catalysis is at least partly an oxidative dehydrogenation.

In the novel gas-phase partial oxidation under heterogeneous catalysis, said $C_3$ precursors of acrylic acid are as a rule diluted with inert gases, such as nitrogen, CO, $CO_2$ and/or steam, are passed, in the form of a mixture with molecular oxygen, at elevated temperatures and, if required, superatmospheric pressure, over transition metal mixed oxide catalysts and converted by oxidation into an acrylic acid-containing product gas mixture.

DE-A 19740252, DE-A 19740253, DE-A 19833049, DE-A 19814375, DE-A 19814421 and DE-A 19814449 disclose that the basic separation of the acrylic acid contained in the product gas mixture from acrylic acid-containing product gas mixtures of gas-phase partial oxidations of $C_3$ precursors of acrylic acid under heterogeneous catalysis is possible by subjecting the product gas mixture, if necessary after direct and/or indirect prior cooling, to a fractional condensation while sending into itself in a separation column provided with baffles having separation activity, and removing the acrylic acid as crude acrylic acid via a side take-off of the separation column. The term crude acrylic acid expresses the fact that the acrylic acid removed via the side take-off is not a pure product but a mixture which also contains typical byproducts of the gas-phase oxidation (e.g. water, lower aldehydes, acetic acid, propionic acid, etc.) in addition to acrylic acid (as a rule $\geq 95\%$ of the weight of the mixture).

Compared with the other known processes for the basic separation of a crude acrylic acid from the product gas mixtures of gas-phase partial oxidations of $C_3$ precursors of acrylic acid under heterogeneous catalysis, which are usually carried out by taking up the acrylic acid in a suitable absorbent and then removing the absorbent by distillative separation methods, the typical feature of the fractional condensation method outlined above is that undesired polymer formation occurs to a lesser extent on addition of polymerization inhibitors.

The abovementioned prior art publications recommend in particular stacked packings, dumped packings and/or trays, preferably bubble trays, sieve trays, valve trays and/or dual-flow trays, as baffles having separation activity in the separation columns to be used for the fractional condensation of the product gas mixture of the gas-phase partial oxidation of $C_3$ precursors of acrylic acid under heterogeneous catalysis. In the exemplary embodiments, the only separation columns used are those which contain either only bubble trays (hydraulically sealed cross-flow trays) or only dual-flow trays as baffles having separation activity. The disadvantage of the prior art recommendations is that stacked packings and dumped packings, on the one hand, promote polymer formation and, on the other hand, rapidly lose their permeability when undesired polymer formation occurs. Another disadvantage, when dual-flow trays are used alone as baffles having separation activity, is that the separation efficiency of the column is not completely satisfactory. When bubble trays are used alone, the separation column loses its permeability as a result of polymer formation even after operating times which are not completely satisfactory.

BRIEF SUMMARY OF THE INVENTION

It is an object of the present invention to provide a process for the fractional condensation of an acrylic acid-containing product gas mixture of a gas-phase partial oxidation of $C_3$ precursors of acrylic acid with molecular oxygen under heterogeneous catalysis in a separation column containing hydraulically sealed cross-flow trays as baffles having separation activity, which process reduces the disadvantages of said prior art processes.

We have found that this object is achieved by a process for the fractional condensation of an acrylic acid-containing product gas mixture of a gas-phase partial oxidation of $C_3$ precursors of acrylic acid with molecular oxygen under heterogeneous catalysis in a separation column containing hydraulically sealed cross-flow trays as baffles having separation activity, wherein the separation column used is one which contains, from bottom to top, first dual-flow trays and then hydraulically sealed cross-flow trays as baffles having separation activity.

BRIEF DESCRIPTION OF THE DRAWING

FIG. 1 is a schematic plan view of the separation column and additional components used for the fractional condensation process described herein.

DETAILED DESCRIPTION OF THE INVENTION

In this document, dual-flow trays are understood as meaning trays having simple passages (holes, slots, etc.). The gas ascending in the column and the reflux liquid descending in the column pass through the same passages while flowing in opposite directions. The cross section of the passages is adapted to the loading of the column in a manner known per se. If it is too small the ascending gas flows through the passages at such a high velocity that the reflux liquid descending in the column is entrained essentially without any separation effect. If the cross section of the passages is too large, ascending gas and descending reflux pass by one another essentially without exchange and the tray is in danger of running dry. Usually, dual-flow trays have no drainpipe which connects them to the next tray. Of course, every dual-flow tray is flush with the column walls. With decreasing column loading, dual-flow trays run dry. A typical feature of hydraulically sealed cross-flow trays is that they cannot become empty when the column is switched off, apart from the tiny emptying hole (its cross section is usually more than 200 times smaller than the total cross section of the passages) which each cross-flow tray has for expediency, i.e., even at low column loadings, hydraulically sealed cross-flow trays have backed-up reflux liquid and are in no danger of running dry. This is because, in contrast to dual-flow trays, the passages of hydraulically sealed cross-flow trays are chimneyless holes.

Rather, each passage opens into a chimney which prevents running dry. Vapor-deflecting hoods (bubble caps) which dip into the backed-up tray liquid are mounted above the chimney. Frequently, the vapor-deflecting hoods are slotted or serrated at their edges (i.e. they have transport slots). The vapor stream ascending through the passage is deflected by the vapor-deflecting hoods and flows parallel to the tray, i.e. transversely to the column, into the backed-up liquid. The vapor bubbles emerging from adjacent bubble caps strike one another and form an effervescent layer. Drainpipes and drain segments which leave the trays, as a rule alternately on the left or right, control the liquid level of the trays—with assistance from weirs—and feed the reflux to the tray underneath. It is important for the hydraulically sealing effect that the drainpipes or drain segments of the upper tray dip into the backed-up liquid of the tray underneath. Preferably, small weirs are present. Bubble caps adjustable in height permit adaptation to the flow conditions and adjustment of the depths of immersion in the event of irregularities during production, so that all bubble caps of the tray have uniform gas flow. Guide plates mounted on the tray guide the liquid, if required, along prescribed paths and provide relative flows between vapor and liquid which are advantageous with respect to the tray efficiency.

Depending on the design and arrangement of the bubble caps, a distinction is made between, for example, round bubble trays (passage, chimney and bubble cap are round), Thormann trays (passage, chimney and bubble cap are rectangular and the trays are arranged one behind the other, the longer edge of the rectangle being at right angles to the liquid flow) and tunnel trays (like Thormann trays except that the longer edge of the rectangle is aligned parallel to the liquid flow).

Typically, the acrylic acid-containing product gas mixture of a gas-phase partial oxidation of $C_3$ precursors of acrylic acid with molecular oxygen under heterogeneous catalysis over solid catalysts has the following composition:

from 1 to 30% by weight of acrylic acid, from 0.05 to 10% by weight of molecular oxygen, from 1 to 30% by weight of water, <5% by weight of acetic acid, <3% by weight of propionic acid, <1% by weight of maleic acid and/or maleic anhydride, <2% by weight of acrolein, <1% by weight of formaldehyde, <1% by weight of furfural, <0.5% by weight of benzaldehyde and <1% by weight of propene, the remaining amount comprising inert gases, e.g. nitrogen, carbon monoxide, carbon dioxide, methane or propane.

The gas-phase oxidation itself can be carried out as described in the prior art. Starting from propane, the gas-phase oxidation can be carried out, for example, in two successive oxidation stages, as described in EP-A 700714 and in EP-A 700893. However, the gas-phase oxidations cited in DE-A 19 740 253 and in DE-A 19 740 252 can of course also be used.

As a rule, the temperature of the product gas mixture (1) leaving the gas-phase oxidation is from 150 to 350° C., frequently from 200 to 300° C. In a quench system 4, the hot product gas mixture (1) is expediently cooled to a temperature of from 100 to 180° C., initially by direct cooling, before it is fed, for the fractional condensation, to the lowermost section of the separation column to be used according to the invention. The operating pressure prevailing in the column is as a rule from 0.5 to 5, frequently from 0.5 to 3, in many cases from 0.5 to 2, bar.

The quench apparatuses used may be any of the apparatuses known for this purpose in the prior art (e.g. spray scrubbers, venturi scrubbers, bubble columns or other apparatuses having sprayed surfaces), venturi scrubbers or spray coolers preferably being used.

For example, bottom liquid from the novel fractional condensation may be used as quench liquid. During the quench, unvaporized quench liquid is expediently circulated, if necessary via a heat exchanger providing indirect cooling. Some of the circulated quench liquid is expediently removed continuously as a high-boiler purge. If required, the acrylic acid oligomers contained in the purge and formed by Michael Addition in a reversible manner can be cleaved by the action of elevated temperatures (from 130 to 250° C.) and, if required, with the addition of acidic or basic cleavage catalysts at reduced pressure to give acrylic acid. The acrylic acid escaping in vapor form is expediently condensed and is recycled to the circulation of the quench liquid.

The point at which the quenched product gas mixture of the catalytic gas-phase oxidation is passed into the separation column to be used according to the invention is expediently located below the lowermost dual-flow tray. In principle, the fractional condensation can be effected inside the column in a manner known per se by indirect cooling and/or heating. However, it is expedient to effect the fractional condensation as follows.

A part of the substances which form and/or condense while the quench product gas mixture is ascending and are more sparingly volatile than acrylic acid is removed via a first collecting tray mounted above the feedpoint and below the lowermost dual-flow tray. Some of the high-boiler fraction removed can be mixed with bottom liquid removed from the column and then used as such as a quench liquid. The remaining portion of the removed high-boiler fraction is cooled or heated in an indirect heat exchanger and recycled to the column above the first collecting tray but below a second collecting tray, mounted in the lower column half. The crude acrylic acid, which usually has a purity of ≧95% by weight, is removed via the second collecting tray in the side take-off as a medium-boiler fraction. Expediently, the crude acrylic acid is fed to other stages for further purification by distillation and/or crystallization, and at least a part of the bottom liquids and/or mother liquors obtained in the distillations and/or crystallizations is recycled to the column below the second, but above the first, collecting tray. Alternatively, the recycling of the bottom liquids and/or mother liquors can also be effected in such a way that they are divided into two part-streams, one of which is recycled to the column below the second, but above the first, collecting tray and the other above the second collecting tray. The last-mentioned of the two part-streams will as a rule be up to 35% by weight, based on the total recycle. Essentially water and components more sparingly volatile than water are condensed from the low-boiler gas stream escaping at the top of the column, expediently by direct cooling in a space free of baffles or containing baffles, by means of a second quench liquid (referred to as quench liquid in this document for differentiation). The condensate obtained is referred to as dilute acid solution. Some of the dilute acid solution is expediently recycled to the top of the column to increase the separation efficiency there. A further part of the dilute acid solution is expediently removed and disposed of (for example incinerated) and the remaining part of the dilute acid solution is usually cooled indirectly in an external heat exchanger and used as a quench liquid.

Those components of the low-boiler stream which are more readily volatile than water are usually taken off essentially in gaseous form and, if required, recycled as diluent gas to the gas-phase oxidation.

Alternatively, the quench in dilute acid solution can be integrated in the column for the fractional condensation. In this case aqueous reflux liquid is removed via a further collecting tray in the upper part of the column, cooled indirectly in a heat exchanger and, apart from the purge fraction to be disposed of, recycled partly to the top of the column and partly below the collecting tray. Any exit gas to be recycled to the gas-phase oxidation leaves the column at its top in this case.

In the novel process, the dual-flow trays in the separation column should expediently extend at least to the side take-off for the crude acrylic acid. In the novel process, however, the dual-flow trays in the separation column preferably extend approximately to that cross section in the separation column from which the acrylic acid contents of the reflux liquid, towards the top of the column, $\geq 20\%$ by weight, based on the weight of the reflux liquid. The number of dual-flow trays for the novel separation process is as a rule from 5 to 60, preferably from 20 to 40. The opening ratio of the dual-flow trays is furthermore expediently from 10 to 25%, preferably from 12 to 20%. The dual-flow trays to be used according to the invention usually have, as passages, circular holes whose diameters are usually from 5 to 50 mm, frequently from 10 to 20 mm. From bottom to top in the separation column, frequently the hole diameters are decreased and/or the number of holes reduced. It is useful if the number of dual-flow trays used for the novel process corresponds to from about 8 to 20, frequently from about 10 to 15, theoretical plates.

The number of hydraulically sealed cross-flow trays following the dual-flow trays is as a rule from 5 to 60, frequently from 15 to 40. Expediently, these trays have transport slots for better forced transport of the liquid via the tray. The opening ratio of the cross-flow trays to be used according to the invention is as a rule from 5 to 25%, frequently from 10 to 20% (the opening ratio expresses the passage cross sections as a percentage of the total cross section). As a rule, the number of hydraulically sealed cross-flow trays for the novel process is such that it corresponds to from about 10 to 30, frequently from about 15 to 25, theoretical plates. Thormann trays are preferably used for the novel process. If the quench in dilute acid solution is integrated in the column for the fractional condensation, in principle all baffle types known from rectification technology are suitable as baffles having separation activity for the novel process for this region of the separation column (acrylic acid content of the reflux liquid, from bottom to top, is as a rule $\leq 10\%$ by weight), i.e. both cross-flow and countercurrent trays, but also dumped packings and stacked packings, can be used in this region of the separation column. The preferred embodiment comprises cross-flow trays designed as valve trays. Valve trays have, for example, holes having plate, ballast or lifting valves (floating flaps) which have a limited stroke and adapt the size of the opening for the passage of vapors to the respective column loading. The ascending vapor stream is deflected, flows parallel to the tray into the backed-up reflux liquid and forms an effervescent layer. Weir-containing drainpipes feed the reflux from tray to tray. The vapor velocity must not fall below a design-related lower loading limit, otherwise the tray liquid flows away.

The inhibition of polymerization in the novel process can be carried out essentially as described in DE-A 19909923. Thus, it can be carried out, for example, by adding, at the top of the condensation column, phenothiazine or a mixture of an N-oxyl radical and a benzene compound which has two substituents bonded via heteroatoms to the aromatic ring and at least one mobile hydrogen.

In a more advantageous form of the inhibition of polymerization, said inhibition is carried out exclusively by means of N-oxyl radicals (for example those stated in EP-A 765 956). These are compounds which have at least one —N—O group.

N-oxyl radicals preferred according to the invention are the pyrrolidin-1-oxyl types and the piperidin-1-oxyl types. Examples are 4,4',4"-tris(2,2,6,6-tetramethylpiperidin-1-oxyl)phosphite, 2,2,6,6-tetramethylpiperidin-1-oxyl (TEMPO), 4-hydroxy-2,2,6,6-tetramethylpiperidin-1-oxyl (4-OH-TEMPO), 4-oxo-2,2,6,6-tetramethylpiperidin-1-oxyl (4-oxo-TEMPO), 4-dimethylamino-2,2,6,6,-tetramethylpiperidin-1-oxyl, 4-amino-2,2,6,6-tetramethylpiperidin-1-oxyl, 4-ethanoyloxy-2,2,6,6-tetramethylpiperidin-1-oxyl, 2,2,5,5-tetramethylpyrrolidin-1-oxyl and 3-amino-2,2,5,5,-tetramethylpyrrolidin-1-oxyl. The N-oxyl inhibitors are preferably used in the form of from 0.1 to 2% strength by weight solutions in water and/or in dilute acid solution. The aqueous N-oxyl inhibitor solution is expediently added in the upper fourth of the condensation column and/or in the quench using dilute acid solution. The aqueous solution may contain only one N-oxyl radical or a mixture of N-oxyl radicals. The addition of an aqueous solution which contains exclusively 4-OH-TEMPO as a polymerization inhibitor is sufficient to achieve adequate inhibition.

The added amount of the N-oxyl inhibitors to be used is expediently such that the high-boiler fraction and bottom liquid removed from the column contain from 1 to 1000 ppm by weight, based on the weight of the high-boiler fraction, of the N-oxyl inhibitors. Since the high-boiler fraction and bottom liquid removed from the column serve as a quench liquid, the quench system is automatically costabilized. If required, the quench system can be costabilized by adding a phenothiazine compound. Suitable phenothiazine compounds are, for example, phenothiazine (PTZ) itself, bis($\alpha$-methylbenzyl)phenothiazine, 3,7-dioctylphenothiazine and bis($\alpha$-dimethylbenzyl)phenothiazine, among which phenothiazine is preferred. The latter applies in particular when 4-OH-TEMPO is concomitantly used or exclusively used for stabilizing the condensation column. Such an addition of phenothiazine may amount to from 1 to 500 ppm by weight, based on the weight of the quench liquid. Such an addition of phenothiazine compound is expediently effected in solution in acrylic acid, preferably in solution in crude acrylic acid removed via the side take-off (typically from 0.1 to 2% strength by weight).

The amount of N-oxyl radicals required for inhibiting polymerization can be reduced by carrying out less demanding stabilization of the dilute acid solution, i.e. stabilization of the quench system, alternatively or in combination with an aqueous solution of at least one benzene compound which has two substituents bonded to the aromatic ring via heteroatoms and at least one mobile hydrogen (for example, those stated in EP-A 765 856), e.g. a phenol compound (typically from 0.1 to 2% strength by weight solution). Suitable phenol compounds of this type are, for example, hydroquinone or methoquinone (p-methoxyphenyl= MEHQ), among which the latter is preferred. This applies in particular when exclusively 4-OH-TEMPO is used in the top region of the column and the quench system is costabilized with PTZ. As a rule, from 1 to 500 ppm by weight, based on the weight of the dilute acid solution, of at least one phenol compound is used for such inhibition of the dilute acid solution.

An alternative inhibition of polymerization comprises adding an aqueous solution of MEHQ at the top of the condensation column and likewise carrying out the inhibition of the dilute acid solution by adding a solution of MEHQ in water and/or in dilute acid solution. In addition, a solution of PTZ in acrylic acid (e.g., crude acrylic acid) is added in the middle part of the condensation column and, if required, in the quench of the product gas mixture (1).

As stated above, the quench system is automatically costabilized through the stabilization of the condensation column and can be costabilized, if required, by adding phenothiazine and/or methoquinone.

The inhibition of polymerization achieved in the quench liquid is as a rule also sufficient, in the case of a cleavage integrated in the novel process, to ensure adequate stability of the purged quench liquid to undesired free radical polymer formation. On the other hand, in the condensation of the acrylic acid-containing vapors escaping in gaseous form during the cleavage, the condenser surfaces are expediently additionally inhibited (the inhibitors contained in the quench liquid cannot as a rule also evaporate). This inhibition of polymerization on the condenser surfaces is advantageously carried out using the same polymerization inhibitors as those used and/or recommended for inhibiting the condensation column.

If, for example, exclusively 4-OH-TEMPO is used for stabilizing the condensation column and the quench in dilute acid solution, it is expedient to stabilize the condenser surfaces also exclusively with 4-OH-TEMPO, expediently dissolved in crude acrylic acid. However, the condenser surfaces can of course also be costabilized or exclusively stabilized by means of PTZ, MEHQ and/or hydroquinone.

The pressure for the cleavage is advantageously from 25 to 600, preferably from 100 to 300, mbar. The cleavage temperature is expediently from 140 to 230° C., preferably from 160 to 200° C. If the cleave is carried out continuously (the novel process is preferably effected continuously), the residence time in the cleavage reactor should be from about 0.5 to 3 hours. The cleavage to be integrated according to the invention can be carried out in a simple manner in a heatable stirred reactor. As described in U.S. Pat. No. 5,733,075 and in DE-A 41 01 879 the cleavage of the acrylic acid oligomers contained in the purged quench system can be carried out without adding specific acidic or basic cleavage catalysts. However, the cleavage is advantageously carried out in the presence of cleavage catalysts. Suitable such catalysts are, for example, dodecylbenzenesulfonic acid, p-toluenesulfonic acid, sulfuric acid or the solid acidic catalysts of JP-A 3-178949.

Particularly in the case of inhibition of polymerization by means of N-oxyl radicals, especially if 4-OH-TEMPO is used as the sole polymerization inhibitor or as a costabilizer of the quench system 1, it is expedient to carry out the cleavage by adding an inorganic salt, the addition of which to an aqueous solution of a strong Brönsted acid shifts the pH of the aqueous solution toward the alkaline, as recommended, for example, by DE-C 2407236. The amount of basic cleavage catalyst to be added is as a rule from 0.1 to 5% by weight, based on the amount of purged quench liquid to be subjected to the cleavage. Examples of cleavage catalysts suitable according to the invention are KOH, $K_2CO_3$, $KHCO_3$, NaOH, $Na_2CO_3$, $NaHCO_3$, LiOH, $Li_2CO_3$ and $CaCO_3$, i.e. suitable cleavage catalysts are in particular the alkali metal and/or alkaline earth metal salts of weak inorganic or organic Brönsted acids, e.g. phosphoric acid, boric acid, carbonic acid, formic acid or acetic acid.

As a rule, integrated cleavage is carried out at $\leq 1$ bar and from 130 to 250° C.

In other words, alkali metal and/or alkaline earth metal phosphates, borates, carbonates, bicarbonates, formates and acetates are therefore particularly suitable as cleavage catalysts.

The cleavage catalysts are preferably chosen so that they are soluble in the purged quench liquid under the cleavage conditions. According to U.S. Pat. No. 4,293,347 the presence of dialkyl phthalates also has an advantageous effect on the relevant cleavage.

In the novel process, the sparingly volatile residue remaining in the cleavage reactor is regularly disposed of, for example incinerated.

At this point, it should also be stated that, if required, an inert organic liquid which has a boiling point higher than that of acrylic acid, keeps the quench liquid fluid, and can be added to the quench liquid. Particularly suitable high-boiling inert organic liquids of this type are those which are recommended in DE-A 21 36 396 and in DE-A 43 08 087. These are essentially liquids whose boiling point at atmospheric pressure is above 160° C. Examples are ethylhexanoic acid, N-methylpyrrolidone, middle oil fractions from paraffin distillation, diphenyl ether, biphenyl or mixtures of the abovementioned liquids, for example a mixture of from 70 to 75% by weight of diphenyl ether and from 25 to 30% by weight of diphenyl. It is advantageous to use a mixture consisting of from 70 to 75% by weight of diphenyl ether and from 25 to 30% by weight of diphenyl and, based on this mixture, from 0.1 to 25% by weight of o-dimethyl phthalate.

In the abovementioned case, at least a portion of the inert organic liquid present is coevaporated during the cleavage. If a portion of the organic liquid remains in the cleavage residue, the latter can be subjected to a working-up in which the solvent present is separated off, for example by distillation, and is recycled to the quench. The remaining high boilers are disposed of.

The quench apparatuses used may be any of the apparatuses known for this purpose in the prior art (e.g. spray scrubbers, venturi scrubbers, bubble columns or other apparatuses having sprayed surfaces), venturi scrubbers or spray coolers preferably being used according to the invention.

All conventional heat exchangers are suitable for indirect cooling or heating of the quench liquid. Tube-bundle heat exchangers, plate-type heat exchangers and air coolers are preferred. The temperature of the quench liquid after leaving the heat exchanger is usually from 70 to 200° C., frequently from 100 to 150° C. Suitable cooling media are air in the case of the corresponding air cooler and cooling liquids, in particular water, in the case of the other cooling apparatuses. The crude acrylic acid removed at the side take-off also contains, as a rule, from 0.1 to 2% by weight of acetic acid,
from 0.5 to 5% by weight of water, from 0.05 to 1% by weight of low molecular weight aldehydes, from 0.001 to 1% by weight of maleic acid and/or its anhydride and from 1 to 500 ppm by weight of a polymerization inhibitor, based in each case on the weight of the crude acrylic acid. The temperature at the bottom of the column is typically from 90 to 130° C., whereas the top temperature is usually from 40 to 80° C., frequently from 50 to 70° C. The temperature at which the crude acrylic acid is removed is generally from 80 to 110° C. The recycling temperature of the high boilers on entering the column is typically from 95 to 115° C. The temperature of the dilute acid solution on recycling to the column is as a rule from 25 to 35° C. In principle, the quench system may be of the same form as the quench system. According to the invention, the crude acrylic acid can of course also be removed via a plurality of collecting trays in succession at short intervals.

The crude acrylic acid removed as a medium-boiler fraction can be fed, for example, to a crystallization stage for further purification. Here, as a rule, no solvent is added, in particular no organic solvent. The crystallization method to be used is not subject to any restrictions. The crystallization can be carried out continuously or batchwise, in one or more stages, to virtually any purities. If required, water can be added to the crude acrylic acid to be purified by crystallization, before the crystallization (up to 10% by weight or more, preferably up to 5% by weight, based on the amount of acrylic acid present). Such an addition facilitates the removal of acetic acid contained as a byproduct in the crude acrylic acid, since said acetic acid is incorporated into the acrylic acid crystals to a lesser extent in the presence of water. Moreover, the presence of water reduces the tendency to encrustation.

It is surprising that a crude acrylic acid suitable for esterification can be obtained from only a single crystallization stage. This crystallization stage is expediently carried out as a suspension crystallization. An advantageously used crystallizer for this purpose is a trough in which wiped cooling plates (through the interior of which the cooling medium flows) are arranged such that they are suspended one behind the other. Formation of layer crystallization is suppressed by the wiping of the cooling plates. The crude acrylic acid is fed (pumped or conveyed with overflow control) continuously through the crystallizer from back to front. The one-phase crude acrylic acid thickens to give a two-phase suspension containing acrylic acid crystals as solid phase. A crystallizer particularly suitable in this respect is a crystallizer from GMF Gouda (Netherlands) of the cooling disk crystallizer type. The crystals formed are expediently isolated from the abovementioned suspension by means of a centrifuge (for example one from Siebtechnik, of the SHS reciprocating centrifuge type with a conical screen drum) and, if required, washed with crude acrylic acid already further purified and/or subjected to sweating, which is described below. The isolation and washing of the suspension crystals can, however, also advantageously be carried out in a scrubber column as described, for example, in EP-A 97405, U.S. Pat. No. 3,872,009, EP-A 98637, EP-A 305316, EP-A 105524 and WO 84/00118. The crystals are then usually introduced into a container which advantageously already contains an amount of molten acrylic acid crystals purified in a corresponding manner. If required, this molten acrylic acid contains added polymerization inhibitor (e.g. MEHQ, PTZ or 4-hydroxy-TEMPO). As a rule, however, the inhibitor residue remaining in the crystals is sufficient for ensuring adequate inhibition. The acrylic acid crystals obtained are then melted by indirect heating. The acrylic acid melt thus obtainable usually has a purity of $\geq 98\%$ by weight and can be marketed directly as acrylic acid suitable for esterification.

Instead of suspension crystallization, it is also possible to use layer crystallization, for example falling-film crystallization, as described, for example, in EP-A 616 998, for obtaining pure acrylic acid. For example, water/methanol, water/ethanol and water/ethylene glycol mixtures are suitable as liquid cooling media/heating media.

To obtain particularly high purities ("pure acrylic acid") the crystallization is expediently carried out as a fractional crystallization. In fractional crystallization, all the stages which produce crystals which are purer than the melt fed in are usually referred to as purification stages. All the other stages are referred to as hot stripping stages. Multistage processes are expediently operated according to the countercurrent principle, in which, after the crystallization in each stage, the crystals are isolated from the mother liquor and these crystals are fed to the respective stage with the next highest purity, while the crystallization residue is fed to the respective stage with the next lowest purity.

The temperature of the solution during the crystallization is advantageously from +5 to +14° C., in particular from +8 to +120° C. The solids content in the crystallizer is advantageously from 0 to 80 g of solid/100 g total mass. In the suspension crystallization, the solids content is preferably from 15 to 35 g of solid/100 g total mass, and in the layer crystallization it is preferably from 50 to 80 g of solid/100 g total mass.

In one possible embodiment of the invention, the crystallization is carried out by cooling apparatus walls and/or by vaporizing the solution under reduced pressure. In the crystallization by cooling, the heat is removed via scraped-surface coolers which are connected to a stirred kettle or a container without a stirrer. Here, the circulation of the crystal suspension is ensured by means of a pump. It is also possible to remove the heat via the wall of a stirred kettle having a stirrer passing close to the wall. A further embodiment in the case of the crystallization by cooling is the use of cooling disk crystallizers, as manufactured, for example, by Gouda (Netherlands). In a further suitable variant of the crystallization by cooling, the heat is removed via conventional heat exchangers (preferably tube-bundle or plate-type heat exchangers). In contrast to scraped-surface coolers, stirred kettles having stirrers passing close to the wall or cooling disk crystallizers, these apparatuses have no means for avoiding crystal layers on the heat-transfer surfaces. If a state in which the heat transmission resistance assumes to a high value owing to crystal layer formation is reached during operation, switching to a second apparatus occurs. During the operating time of the second apparatus, the first apparatus is regenerated (preferably by melting off the crystal layer or flushing the apparatus with molten crystals). If too high a heat transmission resistance is reached in the second apparatus, switching back to the first apparatus occurs, etc. This variant can also be operated with more than two apparatuses alternately. Moreover, the crystallization can be effected by conventional vaporization of the solution under reduced pressure. In a further embodiment of the invention, the crystallization is carried out in apparatuses in which the crystals grow on cooled surfaces in the crystallization apparatus, i.e. are fixed in the apparatus (for example, layer crystallization method (cf. for example EP-A 616998) from Sulzer Chemtech (Switzerland) or static crystallization method (cf. for example FR-A 2668946) from BEFS PROKEM (France)).

As stated above, the acrylic acid crystals obtained are isolated from the remaining mother liquor. In the case of the layer crystallization or of the static crystallization, the separation of the crystals from the mother liquor can be effected in the crystallization or apparatus itself since the crystals are fixed in the apparatus and the mother liquor can be removed by allowing it to run out of the apparatus. The crystals are removed from the crystallization apparatus by melting the crystals and then allowing the melt to run out. In the case of suspension crystallization, all known solid-liquid separation methods are suitable. In a preferred embodiment of the invention, the crystals can be isolated from the mother liquor by filtration and/or centrifuging. Advantageously, the filtration or centrifuging is preceded by preliminary thickening of the suspension, for example by hydrocyclone(s). All known centrifuges which operate batchwise or continuously are suitable for the centrifuging. Reciprocating centrifuges which can be operated in one or more stages are most advantageous. Scroll-conveyor centrifuges or helical-conveyor centrifuges (decanters) are also suitable. Filtration is advantageously carried out by means of suction filters which are operated batchwise or continuously, with or without a stirrer, or by means of belt filters. In general, the filtration can be carried out under super atmospheric or reduced pressure.

During and/or after the solid-liquid separation, further process steps for increasing the purity of the crystals or of the crystal cake can be provided. In a particularly advantageous embodiment of the invention, the isolation of the crystals from the mother liquor is followed by one-stage or multistage washing and/or sweating of the crystals or of the crystal cake. During the washing, the amount of wash liquid is suitably from 0 to 500, preferably from 30 to 200, g of wash liquid/100 g of crystals.

The wash liquid used is not subject to any restrictions. Advantageously, however, washing is effected with pure product, i.e. with a liquid which contains acrylic acid whose purity is the same as or higher than that of the crystal cake to be washed. In addition, washing with water is also possible. Washing can be carried out in apparatuses customary for this purpose.

Scrubber columns (for example from Niro Process Technology B.V. in s'Hertogenbusch (NL)) or those having hydraulic bed transport (for example from TNO in Apeldoorn (NL)), in which the removal of the mother liquor and the washing are carried out in one apparatus, centrifuges which can be operated in one or more stages or suction filters or belt filters are advantageously used. The washing can be carried out on centrifuges or belt filters in one or more stages. Here, the wash liquid can be fed to the crystal cake countercurrent.

Sweating is local melting of contaminated regions. Advantageously, the amount of sweating is from 0 to 80, preferably from 5 to 35, g of molten crystal/100 g of crystals prior to sweating. The sweating is particularly preferably carried out on centrifuges or belt filters and in crystallizers in which the crystals are fixed in the crystallizer (e.g. layer crystallizers). Carrying out a combination of washing and sweating in one apparatus may also be suitable.

After the solid-liquid separation and any further washing and/or sweating, the acrylic acid crystals constitute the purified acid from the process. The purity of the crystals obtained amounts as a rule to from 97 to 99.99% by weight or more of acrylic acid, in particular from 98.5 to 99.9% by weight of acrylic acid. The crystals prepared by the process contain only very small amounts of impurities, such as acetic acid, propionic acid and/or diacrylic acid.

In summary, it may once again be stated that, according to the invention, the crystallization can be realized in principle as a suspension crystallization and/or as a layer crystallization (the crystals which separate out remain fixed in the crystallizer). A suitable crystallization by the latter method is, for example, falling-film crystallization (for example as described in EP-A 616 998), crystallization in a tube with flow through the full cross section (for example according to DE-A 2606364) or static crystallization.

In the suspension crystallization, the cooling can be realized directly (for example evaporation under reduced pressure) and/or indirectly by means of cooled surfaces. Suitable crystallizers for such a suspension crystallization are stirred kettles having stirrers passing close to the wall, scraped-surface coolers and cooling disk crystallizers from Gouda, and circulation crystallization with heat exchangers without an apparatus for avoiding this layer formation is also suitable.

If desired, the purified acid can be esterified by known methods or further purified by known methods.

To increase the yield of acrylic acid, very generally the mother liquor remaining at the end of the crystallization is at least partly recycled, as described at the outset, to the separation column. According to the invention, the proportion of recycled mother liquor is from >0 to 100, preferably from 80 to 100, % by weight, based on the amount of said mother liquor obtained. The recycling of the polymerization inhibitor separated off during the crystallization is ensured simultaneously with the recycling of the mother liquor. This ensures completely satisfactory to inhibition of polymerization with the minimal use of polymerizaiton inhibitors.

According to the invention, molecular oxygen or an inert gas stream containing molecular oxygen can, if required, be passed through the separation column in addition to the product mixture and together therewith. This reinforces the effect of the added polymerization inhibitors.

Of course, the process, this process being for the preparation of methacrylic acid, equivalent to the process described, can be inhibited and operated in a manner corresponding to that described here.

Possible starting compounds for the gas-phase oxidation are isobutene, methyl tert-butyl ether, isobutane, isobutyric acid, tert-butanol, isobutyraldehyde and methacrolein. Otherwise, the statements made in DE-A 19740253 and DE-A 19740252 are applicable in this context.

As described, the inhibition of polymerization in the novel process can also be effected by adding an aqueous MEHQ solution at the top of the column and adding a solution of PTZ in acrylic acid in the middle part of the column. The quench in dilute acid solution is then likewise stabilized by means of aqueous MEHQ solution.

EXAMPLES

Example 1

The Reference Symbols Used in This Example Relate to FIG. 1

A product gas mixture (1) having a temperature of 270° C. and the following composition was obtained from a gas-phase oxidation under heterogeneous catalysis:

11.5% by weight of acrylic acid,
0.3% by weight of acetic acid,
30 ppm by weight of propionic acid,
0.09% by weight of maleic anhydride, 0.01% by weight of acrolein,
0.1% by weight of formaldehyde,
30 ppm by weight of furfural,
0.001% by weight of benzaldehyde,
0.3% by weight of propene,
3.4% by weight of oxygen,
5.3% by weight of water and
1.7% by weight of carbon oxides, the remaining amount comprising $N_2$.

The product gas mixture (1) (3600 g/h) was cooled to 136° C. in a spray cooler (2). The spray liquid used comprised 750 g/h (7) of a total of 7000 g/h of high-boiler fraction (6) removed from the separation column (3) via the collecting tray (5) (at 100° C.) (bottom liquid (4) did not occur). The spray liquid was circulated via the tube-bundle heat exchanger (8) operated with thermal oil. 40 g/h of high boilers were removed (9) continuously from the circulation.

The product gas mixture cooled to 136° C. was fed (10) to the separation column below the collecting tray (5).

The column was a tray column with, as seen from bottom to top, first 25 dual-flow trays and then 50 bubble trays (1 bubble cap per tray). The tray diameter was 49 mm. The dual-flow trays had 6 holes per tray. The hole diameter of the first five dual-flow trays was 9.5 mm. The subsequent 10 trays had a hole diameter of 9 mm and the hole diameter of the last 5 dual-flow trays was 8.7 mm. The tray above tray 15 was in the form of a further collecting tray (11). 1800 g/h of a crude acrylic acid (12) having a temperature of 97° C. and containing

| acrylic acid | 97.3% by weight |
| --- | --- |
| acetic acid | 0.8% by weight |
| propionic acid | 600 ppm by weight |
| furfural | 700 ppm by weight |
| maleic anhydride | 40 ppm by weight |
| benzaldehyde | 200 ppm by weight |
| water | 1.3% by weight | were taken off via said collecting tray and fed to a suspension crystallizer (13). A part (6250 g/h) of the high-boiler fraction (14) removed was heated to 105° C. in a tube-bundle heat exchanger (15) operated with thermal oil and was recycled (16) to the column at the 5th tray.

The crystallizer was a stirred container (3 l interval volume) with a helical ribbon impeller. The heat of crystallization was removed via the double jacket of the container. The equilibrium temperature of the solution was 9.7° C. The suspension produced in the crystallization (solids content about 25% by weight) was separated batchwise into crystals and mother liquor in a centrifuge at 2000 rpm (centrifuge diameter 300 mm) and in a centrifuging time of 3 minutes. The crystals were then washed with molten (previously washed ) crystals (80 g) for 20 seconds at 2000 rpm. The mother liquor, together with the wash liquid, was recycled (28) to the separation column at the 15th tray.

Analysis of the crystals (370 g/h) gave the following contents:

| acrylic acid | 99.5% by weight |
| --- | --- |
| acetic acid | 0.2% by weight |
| propionic acid | 200 ppm by weight |
| maleic anhydride | 20 ppm by weight |
| furfural | 20 ppm by weight |

| -continued | |
| --- | --- |
| benzaldehyde | 5 ppm by weight |
| water | 0.06% by weight |

A gaseous mixture (17) was removed at the top of the column and subjected to partial condensation in the spray cooler (18). 480 g/h of the resulting dilute acid solution (19) were recycled (26) to the top of the column at 30° C. 220 g/h of the dilute acid solution were removed (20) continuously (the dilute acid solution contained 3% by weight of acrylic acid and 2.6% by weight of acetic acid). 90 g/h of the dilute acid solution removed were mixed with MEHQ (22) and, as a 0.5% strength by weight aqueous stabiliser solution (21), together with the remainder of the dilute acid solution (23), cooled to 18° C. via the water-cooled tube-bundle heat exchanger (24) and used as spray liquid (25). Another part of the dilute acid solution removed was used to prepare a 0.5% strength by weight aqueous solution of 4-hydroxy-TEMPO, which was fed (27) in an amount of 18 g/h at a temperature to the separation column at the 75th tray.

The separation apparatus described was operated for 40 days without significant polymer formation.

Comparative Example 1

The Reference Symbols Used in This Example Relate to the Figure Attached to This Document A product gas mixture (1) at 270° C. and having the following composition was obtained from a gas-phase oxidation under heterogeneous catalysis:

11.5% by weight of acrylic acid,
0.3% by weight of acetic acid,
30 ppm by weight of propionic acid,
0.09% by weight of maleic anhydride,
0.1% by weight of acrolein,
0.1% by weight of formaldehyde,
30 ppm by weight of furfural,
0.01% by weight of benzaldehyde,
0.3% by weight of propene,
3.4% by weight of oxygen,
5.3% by weight of water and
1.7% by weight of carbon oxides, the remaining amount comprising $N_2$.

The product gas mixture (3600 g/h) was cooled to 136° C. in a spray cooler (2). The spray liquid used comprised 750 g/h (7) of a total of 7000 g/h of high-boiler fraction (6) removed from the separation column (3) via the collecting tray (5) (at 100° C.) (bottom liquid 4 was not concommitantly used). The spray liquid was circulated via the tube-bundle heat exchanger (8) operated with thermal oil. 40 g/h of high boiler were removed (9) continuously from the circulation.

The product gas mixture cooled to 136° C. was fed (10) to the separation column below the collecting tray (5).

The column was a tray column with 75 dual-flow trays. The tray above tray 15 was in the form of a further collecting tray (11). 1620 g/h of a crude acrylic acid (12) having a temperature of 92° C. and containing

| | |
|---|---|
| acrylic acid | 96.6% by weight |
| acetic acid | 1.9% by weight |
| propionic acid | 430 ppm by weight |
| furfural | 470 ppm by weight |
| maleic anhydride | 40 ppm by weight |
| benzaldehyde | 300 ppm by weight |
| water | 1.2% by weight | were taken off via said collecting tray and fed to a suspension crystallizer (13). A part (7400 g/h) of the high-boiler fraction (14) removed was heated to 100° C. in a tube-bundle heat exchanger (15) operated with thermal oil and was recycled (16) to the column at the 5th tray.

The crystallizer was a stirred container (3 l internal volume) with a helical ribbon impeller. The crystallization heat was removed via the double jacket of the container. The equilibrium temperature of the solution was 9.7° C. The suspension produced in the crystallization (solids content about 22% by weight) was separated batchwise into crystals and mother liquor in a centrifuge at 2000 rpm (centrifuge diameter 300 mm) and in a centrifuging time of 3 minutes. The crystals (360 g/h) were then washed with molten (previously washed) crystals (80 g) for 20 seconds at 2000 rpm. The mother liquor, together with the wash liquid, was recycled (28) to the separation column at the 15th tray.

Analysis of the crystals (330 g/h) gave the following contents:

| | |
|---|---|
| acrylic acid | 99.0% by weight |
| acetic acid | 0.5% by weight |
| propionic acid | 160 ppm by weight |
| maleic anhydride | 20 ppm by weight |
| furfural | 60 ppm by weight |
| benzaldehyde | 30 ppm by weight |
| water | 0.25% by weight |

A gaseous mixture (17) was removed at the top of the column and subjected to partial condensation in the spray cooler (18). 690 g/h of the resulting dilute acid solution (19) were recycled (26) to the top of the column at 30° C. 270 g/h of the dilute acid solution were removed continuously (20) (the dilute acid solution contained 7.9% by weight of acrylic acid and 0.84% by weight of acetic acid). 90 g/h of the dilute acid solution removed were mixed with MEHQ (22) and, as a 0.5% strength by weight aqueous stabiliser solution (21), together with the remainder of the dilute acid solution (23), cooled to 18° C. via the water-cooled tube-bundle heat exchanger (24) and used as spray liquid (25). Another part of the dilute acid solution removed was used to prepare a 0.5% strength by weight aqueous solution of 4-hydroxy-TEMPO, which was fed (27) in an amount of 18 g/h at a temperature to the 75th tray of the separation column.

Comparative Example 2

The procedure was as in comparative example 1. However, the column for the fractional condensation was a tray column with 75 bubble trays. After 26 days, it was necessary to stop operation of the separation apparatus described, owing to blockage by polymer.

We claim:

1. A process for fractional condensation, comprising:
   condensing an acrylic acid-containing product gas mixture of a gas-phase partial oxidation of $C_3$ precursors of acrylic acid with molecular oxygen under heterogeneous catalysis in a separation column containing hydraulically sealed cross-flow trays as baffles having separation activity, wherein the separation column used is one which contains, from bottom to top, first dual-flow trays and then hydraulically sealed cross-flow trays as baffles having separation activity.

2. A separation column which comprises, from bottom to top, first dual-flow trays and then hydraulically sealed cross-flow trays as baffles having separation activity.

3. A separation column according to claim 1, which comprises THORMANN frays as hydraulically sealed cross-flow trays.

4. A separation column according to claim 1, which comprises hydraulically sealed cross-flow rrays with tiny emptying holes; wherein the tiny emptying holes are more than 200 times smaller than the total cross section of the passages.

5. A process of fractional condensation according to claim 1, wherein the $C_3$ precursor of acrylic acid is propane.

6. A process of fractional condensation according to claim 1, wherein the $C_3$ precursor of acrylic acid is propene.

7. A process of fractional condensation according to claim 1, wherein the $C_3$ precursor of acrylic acid is acrolein.

8. A process of fractional condensation according to claim 1, wherein said acrylic acid cobtaining product mixture comprises:
   from 1 to 30% by weight of acrylic acid,
   from 0.05 to 10% by weight of molecular oxygen,
   from 1 to 30% by weight of water,
   <5% by weight of acetic acid,
   <3% by weight of propionic acid,
   <1% by weight of maleic acid and/or maleic anhydride,
   <2% by weight of acrolein,
   <1% by weight of formaldehyde,
   <1% by weight of furfural,
   <0.5% by weight of benzaldehyde and
   <1% by weight of propene,
   wherein the remainder comprises nitrogen, carbon monoxide, carbon dioxide, methane, or propane.

9. A process of fractional condensation according to claim 1, wherein said hydraulically sealed cross-flow trays are selected from the group consisting of round bubble trays, THORMANN trays, and tunnel trays.

10. A process of fractional condensation according to claim 1, wherein the number of said hydraulically sealed cross-flow trays is from 5 to 60.

11. A process of fractional condensation according to claim 1, wherein the number of said hydraulically sealed cross-flow trays is such that it corresponds to from about 10 to 30 theoretical plates.

12. A process of fractional condensation according to claim 1, wherein the opening ratio of said hydraulically sealed cross-flow trays is from 5 to 25%.

13. A process of fractional condensation according to claim 1, wherein tbe number of said dual-flow trays is from 5 to 60.

14. A process of fractional condensation according to claim 1, wherein the number of said dual flow trays is such that it corresponds to from about 8 to 20 theoretical plates.

15. A process of fractional condensation according to claim 1, wherein the opening ratio of said dual-flow trays is from 10 to 25%.

16. A process of fractional condensation according to claim 1, wherein said dual-flow trays in the separation column extend to that cross section in the separrnion column flow which the acrylic acid contents of the reflux liquid, towards the top of the column, is ≤ 20% by weight, based on the weight of the reflux liquid.

17. A process of fractional condensation according to claim 1, wherein said dual-flow trays have circular wholes with diameters from 5 to 50 mm.

18. A process of fractional condensation according to claim , wherein the separation column exhibits a collecting tray.

19. A process of fractional condensation according to claim 1, wherein the operating pressure prevailing in the column is from 0.5 to 5 bar.

* * * * *